US009615747B2

(12) United States Patent
Roth et al.

(10) Patent No.: US 9,615,747 B2
(45) Date of Patent: Apr. 11, 2017

(54) METHOD FOR DETERMINING SKIN GLYCATION

(75) Inventors: Richard C. Roth, Ada, MI (US); Matthew C. DePauw, Greenville, MI (US); Deborah A. O'Toole, Ionia, MI (US)

(73) Assignee: Access Business Group International LLC, Ada, MI (US)

( * ) Notice: Subject to any disclaimer, the term of this patent is extended or adjusted under 35 U.S.C. 154(b) by 1027 days.

(21) Appl. No.: 13/007,698

(22) Filed: Jan. 17, 2011

(65) Prior Publication Data
US 2011/0178411 A1 Jul. 21, 2011

Related U.S. Application Data

(60) Provisional application No. 61/336,199, filed on Jan. 19, 2010.

(51) Int. Cl.
*A61B 6/00* (2006.01)
*A61B 5/00* (2006.01)
*A61K 49/00* (2006.01)

(52) U.S. Cl.
CPC .......... *A61B 5/0059* (2013.01); *A61B 5/0062* (2013.01); *A61B 5/0071* (2013.01); *A61B 5/0075* (2013.01); *A61B 5/443* (2013.01); *A61B 5/4836* (2013.01); *A61K 49/0004* (2013.01)

(58) Field of Classification Search
CPC ... A61B 5/0059; A61B 5/0062; A61B 5/0071; A61B 5/0075; A61B 5/443
See application file for complete search history.

(56) References Cited

U.S. PATENT DOCUMENTS

| 4,930,516 | A   | * | 6/1990  | Alfano et al. ............... 600/477 |
| 7,139,598 | B2  | * | 11/2006 | Hull et al. ................... 600/317 |
| 8,238,993 | B2  | * | 8/2012  | Maynard et al. ............ 600/310 |
| 2002/0016534 | A1 | * | 2/2002 | Trepagnier et al. ......... 600/316 |
| 2003/0138393 | A1 | * | 7/2003 | Pageon ........................ 424/74 |
| 2004/0186363 | A1 |   | 9/2004 | Smit et al. |

(Continued)

FOREIGN PATENT DOCUMENTS

WO    WO2005045393    5/2005

OTHER PUBLICATIONS

Lachin et al, Factors Associated with Diabetes Onset during Metformin Versus Placebo Therapy in the Diabetes Prevention Program, Diabetes, 2007 vol. 56 No. 4, p. 1153-1159.*

(Continued)

*Primary Examiner* — Joseph M Santos Rodriguez
(74) *Attorney, Agent, or Firm* — Warner Norcross & Judd LLP

(57) ABSTRACT

A method for the measurement and analysis of skin fluorescence across multiple subjects. The method includes illuminating each subject with an excitation wavelength, detecting a peak fluorescence level within a corresponding emission wavelength range, determining relative levels of skin glycation for each subject, and evaluating the efficacy of a skin treatment based on the relative levels of skin glycation. The method can include ranking and normalizing the peak fluorescence levels for each subject, and the method is suitable for use in placebo-controlled studies of anti-glycation skin therapies.

16 Claims, 10 Drawing Sheets

EXAMPLE: METHOD FLOW & ANALYSIS

(56) References Cited

U.S. PATENT DOCUMENTS

2005/0203355 A1\* 9/2005 Stamatas .............. A61B 5/0059
 600/317
2010/0003664 A1 1/2010 Reinisch

OTHER PUBLICATIONS http://web.archive.org/web/20081218212332/http://en.wikipedia.org/wiki/Ranking.\*
Haus et al, Collagen, cross-linking, and advanced glycation end products in aging human skeletal muscle, J Appl Physiol (1985). Dec. 2007;103(6):2068-76. Epub Sep. 27, 2007.\*
Wikipedia, http://web.archive.org/web/20081218212332/http://en.wikipedia.org/wiki/Ranking, Dec. 18, 2008.\*
The university of Cambridge, Collagen Glycation and Diabetes, http://www.ch.cam.ac.uk/group/duer/research/collagen-glycation-and-diabetes).\*
Alzheimer Europe, Phases of clinical trials, http://www.alzheimer-europe.org/Research/Understanding-dementia-research/Clinical-trials/Phases-of-clinical-trials, Oct. 2009, pp. 1-4.\*
https://www.google.com/search?q=define+detect&oq=define+detect&aqs=chrome..69i57j0l5.3583j0j4&sourceid=chrome&es_sm=122&ie=UTF-8.\*

\* cited by examiner

EXAMPLE: METHOD FLOW & ANALYSIS

NORMALIZED RANKING
RELATIONSHIPS PER SUBJECT

| | | | | | | |
|---|---|---|---|---|---|---|
| 1 | 24 | 24 | 24 | 46 | 24 | 46 |
| 2 | 14 | 14 | 14 | 35 | 14 | 35 |
| 3 | 56 | 56 | 56 | 25 | 56 | 25 |
| 4 | 12 | 12 | 12 | 16 | 12 | 16 |
| 5 | 36 | 36 | 36 | 23 | 36 | 23 |
| 6 | 35 | 35 | 35 | 14 | 35 | 14 |

PRIMARY
RELATIONSHIPS
  124  A
  124  A
  356  B
  124  A
  356  B
  356  B

ACCUMULATED RELATIONSHIPS

| | 1 | 2 | 3 | 4 | 5 | 6 |
|---|---|---|---|---|---|---|
| 1 |   | 4 |   | 6 |   | 2 |
| 2 | 4 |   | 2 | 4 | 2 |   |
| 3 |   | 2 |   |   | 6 | 4 |
| 4 | 6 | 4 |   |   |   | 2 |
| 5 |   | 2 | 6 |   |   | 4 |
| 6 | 2 |   | 4 | 2 | 4 |   |

MINOR RELATIONSHIPS HIGHLIGHTED
WITH DOTTED LINE

Fig. 2E

METHOD FOR DETERMINING SKIN GLYCATION

BACKGROUND OF THE INVENTION

The present invention relates to systems and methods to determine the extent of skin glycation, and more particularly to systems and methods to evaluate treatments based on glycation in the human skin.

Glycation is a naturally occurring interaction between sugars and proteins in the human body, the product of which includes glycated proteins. Over time, glycated proteins are chemically modified to form Advanced Glycation End-products (AGEs), which bond with normal proteins to form covalent crosslinks. This crosslinking stiffens formerly flexible or elastic tissue. For example, crosslinking contributes to the wrinkling of the skin, the hardening of arteries and the stiffening of joints. In addition, the accumulation of glycated proteins and AGEs in the skin can be indicative of or correspond to certain types of vascular disease, arthritis, complications of diabetes, cataracts, or other diseases related to aging. Accordingly, skin glycation measuring methods have been used to screen for a variety of diseases and conditions.

In one known method for measuring skin glycation, subjects undergo a tissue biopsy for subsequent chemical extraction and evaluation. In this method, the extracted skin is embedded, sectioned, specially stained, and microscopically examined for glycation crosslinking. Such an invasive method has apparent drawbacks, however, and is poorly suited for evaluation of multiple subject populations. Accordingly, there remains a need for improved systems and methods for measuring skin glycation. In addition, there remains a need for improved, low-cost systems and methods for determining the effectiveness of glycation-breaking or glycation-preventing ingredients across a wide range of skin care therapies.

SUMMARY OF THE INVENTION

A method of detecting relative levels of skin glycation is provided. The method includes providing one or more areas of skin on each of multiple of subjects, radiating the one or more areas of skin across an excitation wavelength range, detecting a peak fluorescence level of the skin within a corresponding emission wavelength range, and determining relative levels of skin glycation based on peak skin fluorescence within the excitation and/or emission wavelength range.

In one embodiment, an excitation wavelength range is between 285-310 nanometers (nm), and the corresponding emission wavelength range is between 330-365 nm. In another embodiment, an excitation wavelength range is between 325-350 nm, and the corresponding emission wavelength range is between 375-405 nm. In still another embodiment, an excitation wavelength range is between 330-370 nm, and the corresponding emission wavelength range is between 415-440 nm. In yet another embodiment, an excitation wavelength range is between 345-385 nm, and the corresponding emission wavelength range is between 450-475 nm.

In even another embodiment, a peak fluorescence within an emission wavelength range proportionately increases with increased glycation. In a further embodiment, a peak fluorescence within an emission wavelength range proportionately decreases with increased glycation.

In still a further embodiment, a peak fluorescence within a first emission wavelength range proportionately decreases with increased glycation, and a peak fluorescence within a second emission wavelength range proportionately increases with increased glycation.

In yet another embodiment, a method is provided for determining the efficacy of an anti-glycation skin treatment. The method includes detecting skin fluorescence for each of multiple subjects, wherein at least one of the multiple subjects received the anti-glycation skin treatment, normalizing and ranking relative skin fluorescence for each of the multiple subjects, and evaluating the efficacy of the skin treatment based, at least in part, on the normalized and ranked skin fluorescence levels for each of the multiple subjects. In even a further embodiment the anti-glycation skin treatment is in a topical form. In another, further embodiment, the anti-glycation skin treatment is included in an oral supplement.

The present method can be used to analyze the effect of multiple ingredients, individually or in a blended condition, on skin glycation. The ingredients can be categorized or classified based on the method and further analysis. Certain ingredients can be selected and included in a formulation or a treatment designed to break up, prevent or otherwise treat glycation of the subjects. Moreover, the method is suitable for ingredient selection and evaluation without performing a biopsy analysis of each subject, and can utilize a mathematical evaluation grid to identify proximity patterns among subjects. The method also permits the use of wider populations and limits or eliminates invasive techniques to evaluate glycation and/or the reduction of glycation.

These and other advantages and features of the present invention will be more fully understood and appreciated in view of the description of the current embodiments and the drawings.

BRIEF DESCRIPTION OF THE DRAWINGS

FIGS. 2A-2E are tables, graphs and evaluation grids illustrating proximity relationships in the fluorescent acquisition of multiple human subjects.

DESCRIPTION OF THE CURRENT EMBODIMENTS

Figure 1:
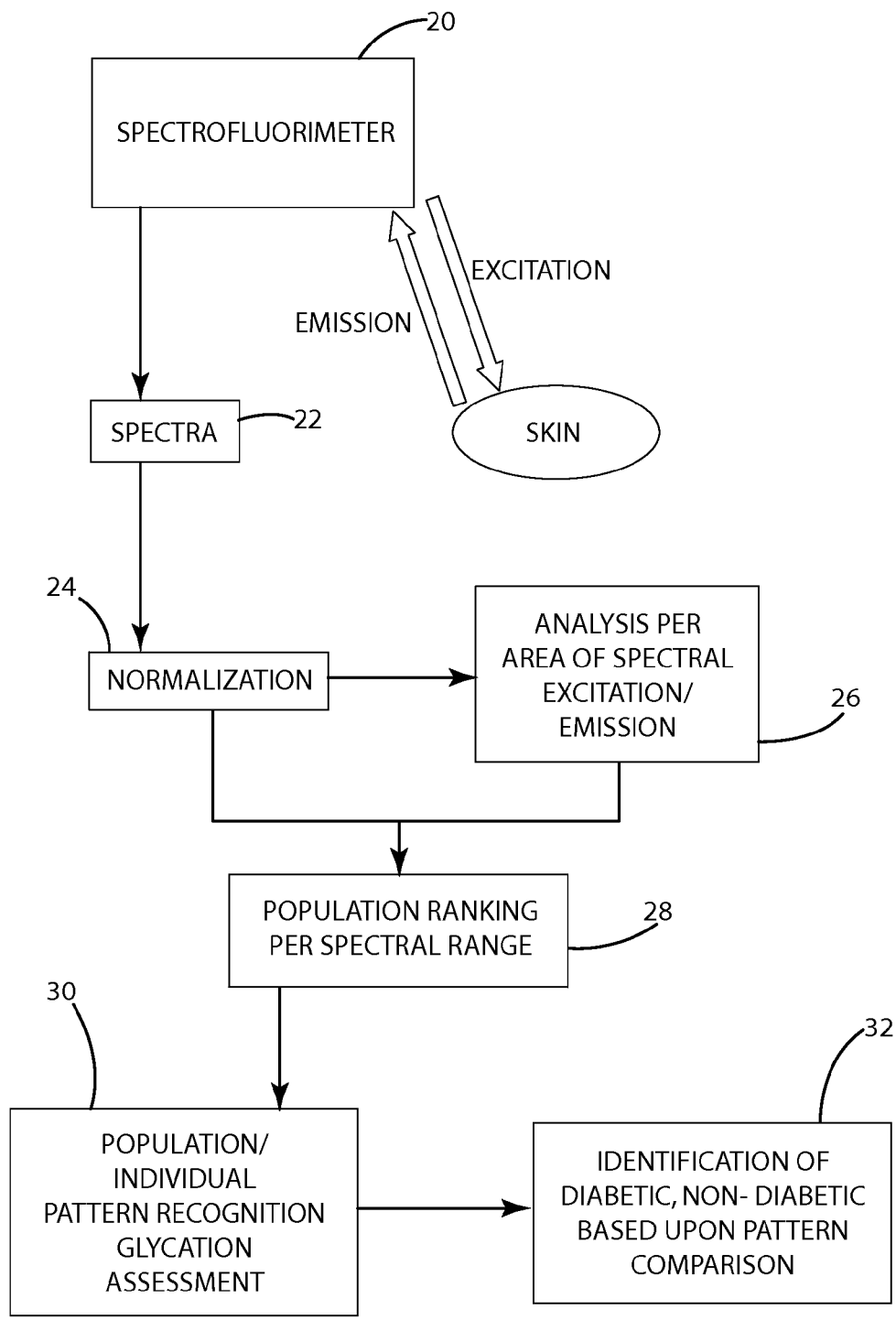
FIG. 1 is a flow diagram illustrating a method for evaluating skin glycation in accordance with an embodiment of the present invention.

The current embodiments relate to an analysis of the fluorescent spectra of the skin, optionally for the purpose of evaluating and selecting formulation ingredients in skin topical applications. Part I of the present disclosure includes methods for measuring a change in skin fluorescence associated with crosslinking of glycated collagen. Part II of the present disclosure includes methods for the mathematical evaluation of the skin fluorescence intensity patterns of multiple subjects.

I. Spectral Acquisition

In one embodiment, a method is disclosed for evaluating a change in skin fluorescence associated with crosslinking of glycated collagen, in which skin fluorescence is measured using a fiber-optic spectrofluorimeter probe, and specific wavelengths are analyzed for fluorescent intensity.

The method can begin with the selection and preparation of the skin sample area. The sample area generally is free from intense skin discoloration and obvious spectral dissimilarities, including moles, scars, abrasions, cuts, major veins, and visual dermal surface irregularities. The skin sites on the subject under test can be evaluated for equivalency on both the left and the right sides of the intended site, and within a skin site 1-2 cm proximate to the intended site.

After the sample area is selected, the skin is prepared for spectral acquisition. The step of preparing a surface area of the skin can include removing hair from the sample area, and optionally washing the skin surface with a mixture of soap and water free of fluorescent agents, or some other suitable cleaning formulation. After the mixture is rinsed from the skin, the skin can air dry and acclimate to the testing environment, optionally for a minimum of thirty minutes. Shortly before subjecting the skin area to excitation light, the skin area can be exposed to ambient, optionally controlled air, and cleaned of any and all lint from clothing. Because lint can interfere with fluorescence measurements, the skin area is thoroughly blown free of lint, optionally using a commercially available compressed air with a fine orifice extension tip, for example.

After the skin site is selected and prepared, a fiber-optic spectrofluorometer, or other suitable instrument, is provided for spectral evaluation of the skin surface area. A suitable spectrofluorometer can be a SKINSKAN® spectrofluorometer, commercial available from Jobin-Yvon, Inc., of Edison, N.J., though other instruments can also be used. This step can include cleaning the fiber optic probe with a commercially available isopropyl alcohol (70-90%), and allowing the probe to air dry with the exposed fiber optic tip oriented in the downward direction. The probe can be inserted within a supportive cylindrical holder to limit extraneous stray light from entering the probe during spectral acquisition. The holder can be constructed of a black non-fluorescing material with a smooth application surface. The diameter of the holder can be sufficiently narrow to eliminate stray light, and can be sufficiently large to significantly reduce localized pressure differentials associated with the application of the probe to the skin. Generally, the probe is oriented within the holder in either a frontal flat surface orientation or a recessed orientation. In the frontal flat surface orientation, the probe tip is maintained flush with the leading surface of the holder. In the recessed orientation, the probe is recessed within the holder a predetermined distance from the skin. The holder can be machined or otherwise configured such that the distance between the probe and the skin is reproducible for every measurement.

The spectrofluorometer is next placed proximate the intended target for measurement. Specifically, the probe may be placed at different levels at or above the skin depending on whether the epidermis or the dermis is the intended target. If the dermis is the intended target, the probe is generally held at the surface of the skin. Optionally, the probe can be held perpendicular to the skin and/or perpendicular to the tangential surface of the closest underlying bone structure. The pressure on the probe generally can be sufficient to prevent movement of the holder while minimizing any potential marking or deformation of the skin from the pressure and shape of the holder. Generally, the entire surface of the holder can evenly contact the skin.

Because skin can transmit and refract light, light originating from the local environment may still pose an indirect detection interference. If desired, to mitigate such indirect light interference, a wrapping can conceal the probe-holder assembly and/or the surrounding area of skin, optionally including a soft thick black cloth that has had residual lint removed with the application and removal of a non-fluorescing adhesive tape. The fluorescence of the cloth can be tested with the fiber-optic spectrofluorometer probe, in the same manner as the skin, to ensure no or only a negligible fluorescent response over the entire experimental range and set of instrumental conditions.

The spectrofluorometer can be set up for use. For example, the spectrofluorometer settings can be based upon the subject population under study. As an initial concern, the acquired data normally is within acceptable instrument acquisition ranges for all wavelengths selected, for all subjects, and for all subject study skin sites. Generally, the acquired fluorescent intensity does not exceed the instrument limitations within the spectral regions of interest, and does not exceed the instrument limitations at intermediate spectral regions between the primary spectral regions of interest. Calibrating the spectrofluorometer can include selecting the acquisition dwell time (accumulation time per excitation-emission wavelength pair) and the photomultiplier voltage. These values can be selected for the specific spectral ranges at which the absorption-emission maxima are expected. That is, the acquisition dwell time and the photomultiplier voltage normally do not exceed the counting abilities of the detector for the skin test site, as "over-range data" typically is unacceptable within the fluorescent spectral region of interest.

Generally, the spectral ranges (excitation (EX) and emission (EM)) are minimized to save time and analysis. The dwell time (acquisition time) is maximized in combination with the detector sensitivity to provide for the greatest fluorescent intensity while optimized to prevent overage to the detector for all subjects, sites, and wavelengths at all test conditions. For example, a fiber-optic spectrofluorometer can be configured with an acquisition time of between 0.05 and 0.2 seconds and a detector voltage of between 650 to 950 V, with optimized conditions of 0.1 seconds and 800V over the range 260-480 nm (EX) and 300-540 nm (EM). The wavelength incrementation can be between 1 nm and 20 nm and preferentially between 2 nm and 5 nm for EX and EM spectra. The wavelengths selected for analysis may consist of specific wavelengths, wavelength ranges or a combination thereof for both excitation and emission. Optionally, the ranges selected are evaluated to provide the maximum fluorescent value within a given region, rather than the fluorescence intensity at a specified single wavelength. While measurement at a specific selected wavelength is acceptable, small variations in subjects, and the instrument, may shift the maximum fluorescent intensity by several nanometers.

The above instrumental parameters are exemplary and may be varied depending on the intent of the test and the subject skin sites of interest. The instrumental parameters also may be varied to accommodate the variety of skin types and skin colorations of subjects. However, the instrumental parameters may generally not be varied within a clinical study without loss of equivalence, unless the study is designed for such variation. The advantages of the present method are maintained by selective definition of the spectral ranges of interest, the selective definition of wavelength increment, the selective determination and use of dwell time, and the optimization of the dwell time and photomultiplier voltage. The spectral range selection can be extremely helpful to the interpretation of results and secondarily extremely helpful to subject analysis time and mathematical analysis time. A selection of too many or too few ranges may impact the ability to identify patterns. In some case, a further loss of advantage can be based upon the selection of the skin site, the emission fluorescent intensity within the spectral range selected, which also impact the reproducibility of the disclosed method.

Once the spectrofluorometer probe is calibrated, spectral acquisition is initiated according to a predetermined excitation and emission wavelength pairing. In one example, the excitation and emission of light from the skin can be obtained over the range 230-700 nm (excitation) and 230-700 nm (emission), optionally with a range from 260-480 nm (excitation) and 300-540 nm (emission). In other applications, the excitation and emission pairings can include: 285-310 nm (excitation) and 330-365 nm (emission); 325-350 nm (excitation) and 375-405 nm (emission); 330-370 nm (excitation) and 415-440 nm (emission); and/or 345-385 nm (excitation) and 450-475 (emission).

The disclosed wavelength ranges, however, are exemplary, and the spectral wavelengths for excitation-emission can be selected based on a number of factors. For example, the excitation-emission wavelength pairings can be selected from among skin fluorescence spectral regions exhibiting the greatest standard deviation from the subject population mean, and from ranges that avoid intense reflections. Also, the excitation-emission wavelength pairings can be selected to correspond to the absorption-emission ranges of the skin fluorophores under study. In addition, the excitation-emission wavelength pairings can be selected based on the absorption-emission ranges of the skin fluorophores that are expected to change as a result of the inclusion of an active ingredient for skin glycation. For example, the wavelengths pairings can include an emission wavelength corresponding to fluorophores of AGEs and/or glycated proteins whose emitted energy is expected to change as a result of skin treatment. Such a skin treatment can include ingredients designed to break-up, prevent or otherwise treat glycation in the skin, and therefore alter the intensity of emitted light. The selection of the spectral ranges for excitation and emission are also optionally chosen from ranges that include the greatest emission wavelength region, and a region that will not typically alter in fluorescent intensity or that is equivalent to and maintained at fluorescent baseline throughout the study. Both individual wavelengths and small localized spectral ranges of interest may be selected.

While noted above as operating over single excitation range, the spectrofluorometer can incrementally scan multiple sub-regions within the identified excitation range. For example, the scan functionality of the instrument, or the programmed scan regions, can include the fluorescent regions of interest while incrementing or decrementing the scan to avoid spectral regions of intense reflection. Optionally, the scanned regions of interest are selected from a group of several smaller spectral regions, or from a specific group of selected excitation-emission wavelength ranges. The spectral acquisition may be accomplished through scanning broad regions of interest or through acquisitions at multiple specific regions of interest. The source of excitation light can be either a broad wavelength source adjusted to specific wavelengths through the use of a monochromator or filter, or a regulated source providing monochromatic excitation source light at specific wavelength or minimal wavelength ranges.

The spectrofluorometer output (e.g., the scanned fluorescent spectra) can be combined and examined in a spreadsheet format. The spreadsheet can typically include the intensity of the reflected (i.e., emitted) light as a function of either the emission wavelength, the excitation wavelength, or both, for example. Spectral regions exhibiting reflection, or the effects of grating overtone reflections, can be eliminated by replacement with the averaged fluorescence intensity derived from a non-fluorescing region of the same spectrum. That is, the region near reflection and non-first order grating effects can be counter-filled with a neutral background fluorescence value obtained from a non-fluorescent region of the spectrum. This counter-filling provides the baseline fluorescence value that serves as a general background.

Figure 7:
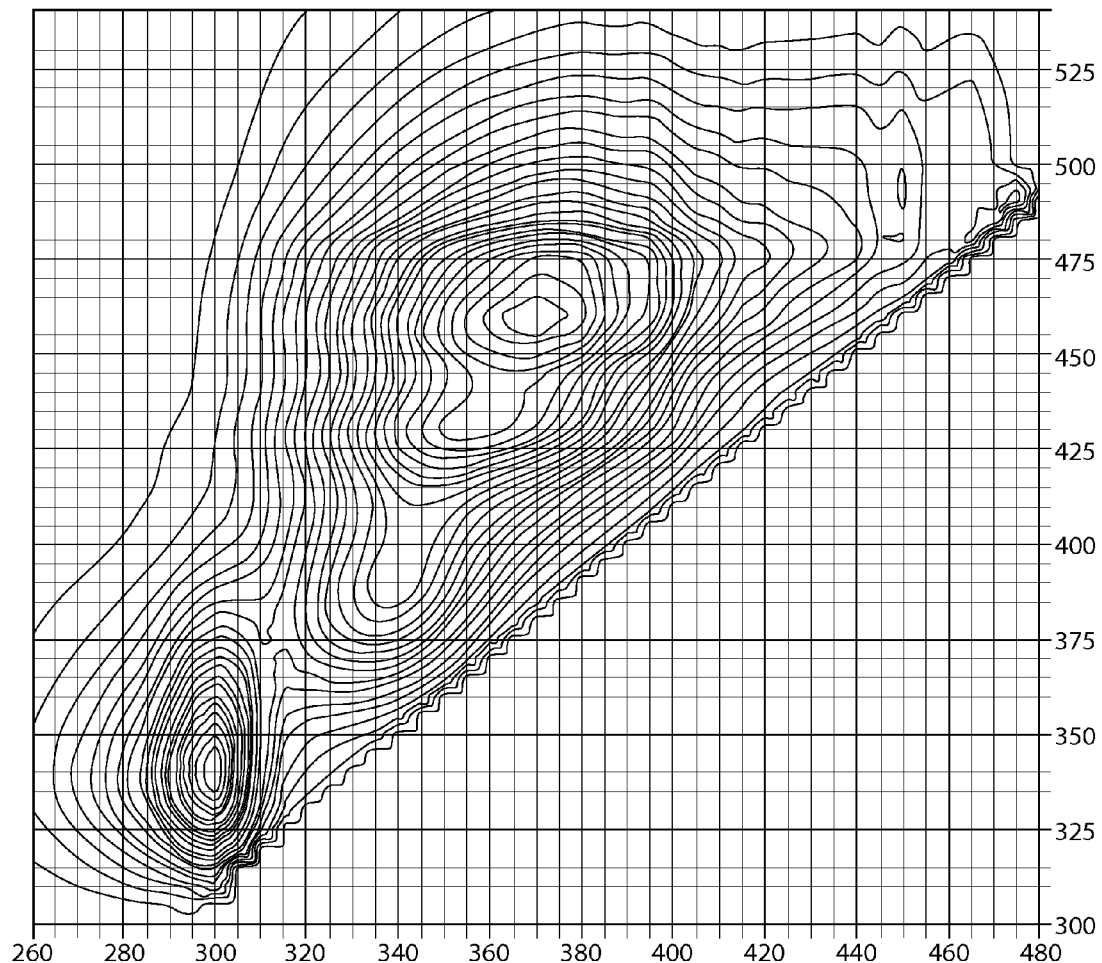
FIG. 7 is a three-dimensional false color plot illustrating the spectral acquisition of human skin under optimal conditions.

In order to interpret data from within the spreadsheet, those regions not scanned and outside the normal fluorescent mode ($\lambda_{em} > \lambda_{ex}$) can be adjusted to provide the same baseline fluorescence value. The overall examination of the remaining data can provide an indication of regions of increased fluorescent intensity against the baseline fluorescence. The minimal fluorescence from the entire spectrum is subsequently subtracted from each excitation-emission. The resulting skin fluorescence intensity, as a relative fluorescence at each excitation (x-value)—emission (y-value) wavelength pair, may be observed both as a 3D topographical false color map (excitation wavelength vs. emission wavelength with contour representing the z-value), and as a 2D false color map (excitation wavelength vs. emission wavelength as shown in FIG. 7) including relative fluorescence (z-value) with a spreadsheet program. Many such commercially available programs, such as Microsoft Excel, contain the capability to depict the spectrofluorometer output as a smoothed curve topographical false color map.

The method as set forth above can be repeated over multiple subjects for the purpose of evaluating and selecting formulation ingredients in skin treatments. For example, the method can be repeated as part of a randomized control trial for a skin treatment, or as part of a placebo controlled study for a skin treatment. At least one test subject can receive the skin treatment being evaluated, while the remaining test subject or subjects receive a placebo treatment designed to have no effect on glycation crosslinking. The skin treatment can include a topical application or an oral supplement. In addition, the skin treatment can include a single ingredient under evaluation, or can include a combination of ingredients under evaluation. Based on an evaluation of the spectrofluorometer output of multiple test subjects, the efficacy of the skin treatment can be evaluated. If recipients of a trial skin treatment are shown to have reduced levels of cross-linking based on a ranking of normalized fluorescence levels, the skin treatment may be shown to be effective. However, if recipients of a skin treatment demonstrate no improvement based on a ranking of normalized fluorescent levels, the skin treatment may be shown to be ineffective. The resulting spectral data from such a study can be analyzed in the manner set forth in Part II below.

II. Spectral Analysis

To assist in correlating skin glycation with one or more criteria among a population of subjects, a method is disclosed in which the peak emission spectra for a plurality of subjects is normalized and ranked. The method can assist in evaluating the efficacy of a skin treatment based on normalized levels of skin glycation. For example, the method can include evaluating the efficacy of a skin treatment based on a change in skin glycation over the course of a treatment regimen.

Referring now to FIG. 1, a flow chart illustrating a method for analyzing the collected fluorescent data for multiple subjects is shown. At step 20, fluorescent excitation-emission data is collected from the skin of multiple subjects substantially as described above in connection with Part I. At step 22, the peak fluorescence for a given emission wavelength range is derived for each subject. These values can be normalized at step 24 and can be repeated for each additional emission wavelength range as shown in step 26. The emission regions selected for comparative and numerical evaluation are normally among those regions identified in literature as associated with glycation cross-linking. In addition, the emission regions selected for evaluation are normally among those regions identified as containing the greatest change as demonstrated from laboratory glycation of ex vivo specimens.

At step 28, each of the normalized emission spectra is ranked by order of intensity. That is, normalized data (regional x, y, z values) are mathematically ranked greatest to least as relative normalized intensity. Normalization is calculated for each region of interest selected and applied for all regions. For instance, if six spectral regions are selected, six separate normalizations are determined from which six normalized value sets are obtained, for a total of 30 normalized data sets. The values obtained for the primary normalized data set undergoing calculation are set to unity.

At step 30, the individual glycation levels for each subject are assessed based on the ranking of step 28. The step can include determining proximity relationships for each subject. The proximity relationships can be selected from proportional normalized intensity based on one or more of the following: numerical rank, percentage rank, percentage proximity, and numerical proximity. Concomitantly, reverse relationships represented by least to greatest intensity are categorized into classes based upon number of similarly ranked associations. Within this specific context there are optionally four selected ranges (excitation-emission wavelength ranges) that are ranked mathematically, although there could be as few as one and perhaps as many as eight ranges employed for ranking and relationship proximity comparison. Through the use of computer algorithms, multiple synergistic relationships may be investigated so that secondary relationships may also be determined and ranked for underlying lower order associations.

At step 32, a similar data set obtained from a known identity group may serve as a training data set for comparison of the obtained spectra. Similarly, spectra from control sites per subject, before, during, and after application; modified application techniques; formulations; and population demographic classes may be utilized to examine the effects of an ingredient. For example, classifications or differences in skin glycation as observable through fluorescence associated with collagen (e.g., such as those associated with the differences observed between populations with a diabetic condition and those considered normal as measured by Hb1ac tests and blood glucose tests) may be differentiated at step 32 without an invasive screening test.

The above method may be used to examine the acceptability of an ingredient, formulation, application technique, clinical trial design, as well as selection of spectral regions of interest. In some instances, the above method may utilize invasive data as a training set (for example, blood sugar level, biopsy). The training set may or may not be required based upon the selected population, body site, testing history, and level of results required for ingredient selection. For example, correlative association, literature, or subject files may provide sufficient information for identification within the training data set, eliminating the need for any invasive reference training set.

Figure 2A:
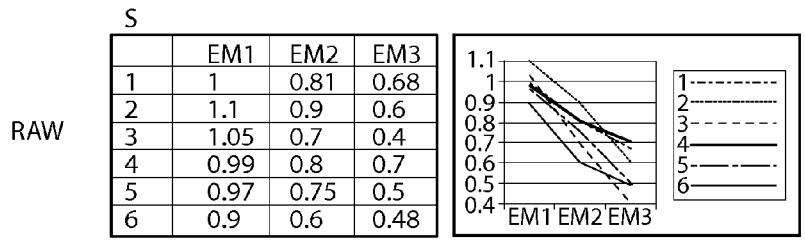
Figure 2B:
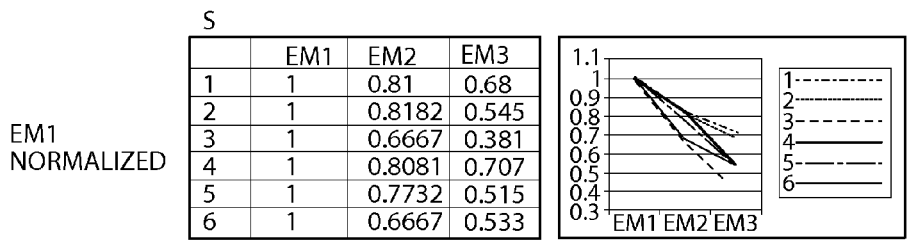
Figure 2C:
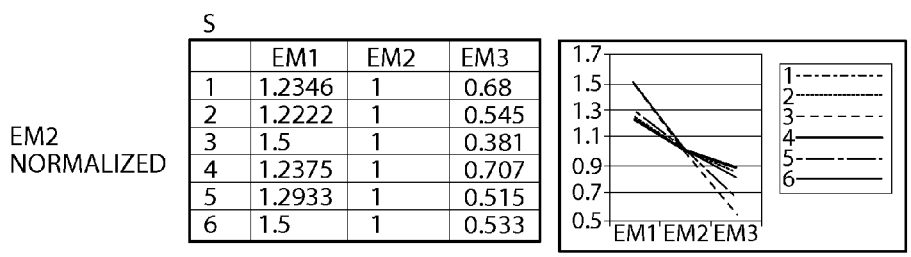
Figure 2D:
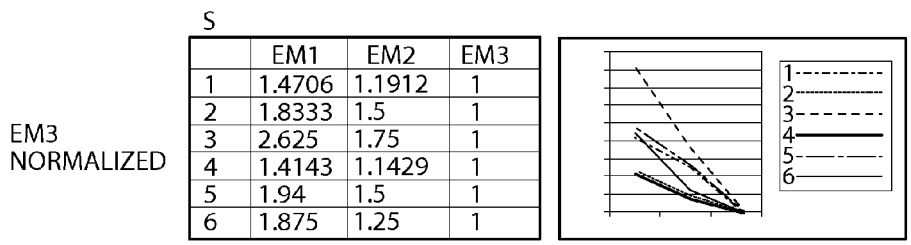

The method discussed above in connection with FIG. 1 can be further understood in connection with FIGS. 2A-2E, relating to a spectral acquisition for six subjects at three excitation-emission wavelength pairings. FIGS. 2A-2E present primary raw data, three normalized data sets, six rankings, a ranking profile and a pattern evaluation grid. The primary raw data of the spectral acquisition is shown in FIG. 2A. The emission wavelengths em1, em2 and em3 are selected to correspond to the fluorescing regions for glycated collagen. As also shown in FIG. 2A, peak fluorescence is plotted for each emission wavelength range and for each of the six subjects. These peak fluorescence values are normalized in FIGS. 2B-2D for each emission wavelength range as discussed above in connection with step 24. FIGS. 2B-2D also reveal the ranking profile for each normalized data set. For example, FIG. 2B includes a ranking table (normalized for em1), in which the leading peak fluorescence (s=1) relates to the second subject at em2 and the fourth subject at em3. In like manner, the lowest peak fluorescence (s=6) relates to the sixth subject for em2 and the third subject for em3.

A Normalized Ranking Relationship table, an Accumulated Relationships table and a Primary Relationship table are shown in FIG. 2E. Both the Normalized Ranking Relationship table and the Accumulated Relationships table indicate the proximity relationships between subjects (50th percentile). For example, subject 1 and subject 2 share a proximity relationship a total of four times, denoted by the number of times "12" is identified in the Normalized Ranking Relationship table. In like manner, subject 1 and subject 4 share a proximity relationship a total of six times, denoted by the number of times "14" is identified in the Normalized Ranking Relationship table. The primary relationships are illustrated in the Primary Relationships table, in which only the main relationship groups (1,2,4) and (3,5,6) are shown. The mathematical evaluation grids of FIG. 2E can therefore assist in identifying patterns in the initial and final states of the skin sites of the subject population during a treatment regimen within individual ingredients or a blended combination of ingredients. For example, the grids of FIG. 2E may assist in detecting relative levels of skin glycation in each of the test subjects, and may assist in evaluating the efficacy of a skin treatment from a comparison of skin glycation levels among test subjects.

The normalization noted above can be conducted for each paired absorption-emission region separately. In addition, the rankings for association are initially dependent only upon the single individual absorption-emission region. The number of associations between each site/population are subsequently accumulated and the resulting patterns are determined (e.g., high-low, a vs. b, crosslinked vs. non-cross-linked). A combined relationship plot including all summed associations can then be determined for each site, location, application-type, or participant, for example. Corroborative determination is dependent, where available, on information providing true identity and conditions of the subjects, sites, and products or ingredients.

The fluorescent spectra obtained according to the method disclosed in Part I above may be analyzed as raw data or may be modified mathematically to exclude the effects of reflection. Specifically, the fluorescent spectra for each subject may be linearly normalized to take into account individual skin fluorescent intensity variations. The effect of an ingredient on the skin may vary based upon the intensity of the absorptions and emissions. Changes or spectral differences between study points may likewise be analyzed through a linearly normalized format. The changes or spectral differences between study points can include: between no application and formula application, between formula applications, and/or between controls or controls and formula applications.

Figure 3:
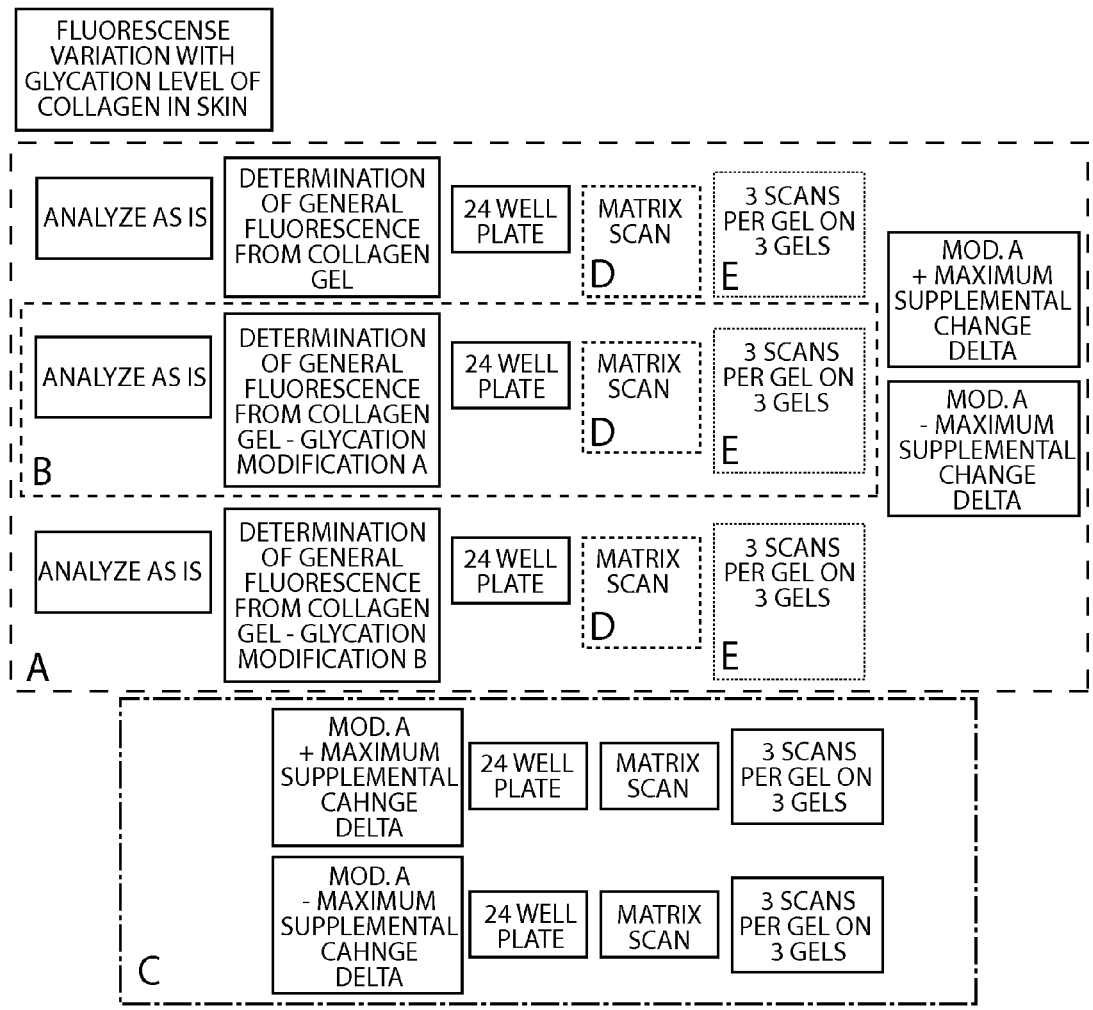
FIG. 3 is a schematic representation of a method for evaluating levels of glycation in collagen gels including a determination of the fluorescent response among multiple collagen gels.
Figure 4:
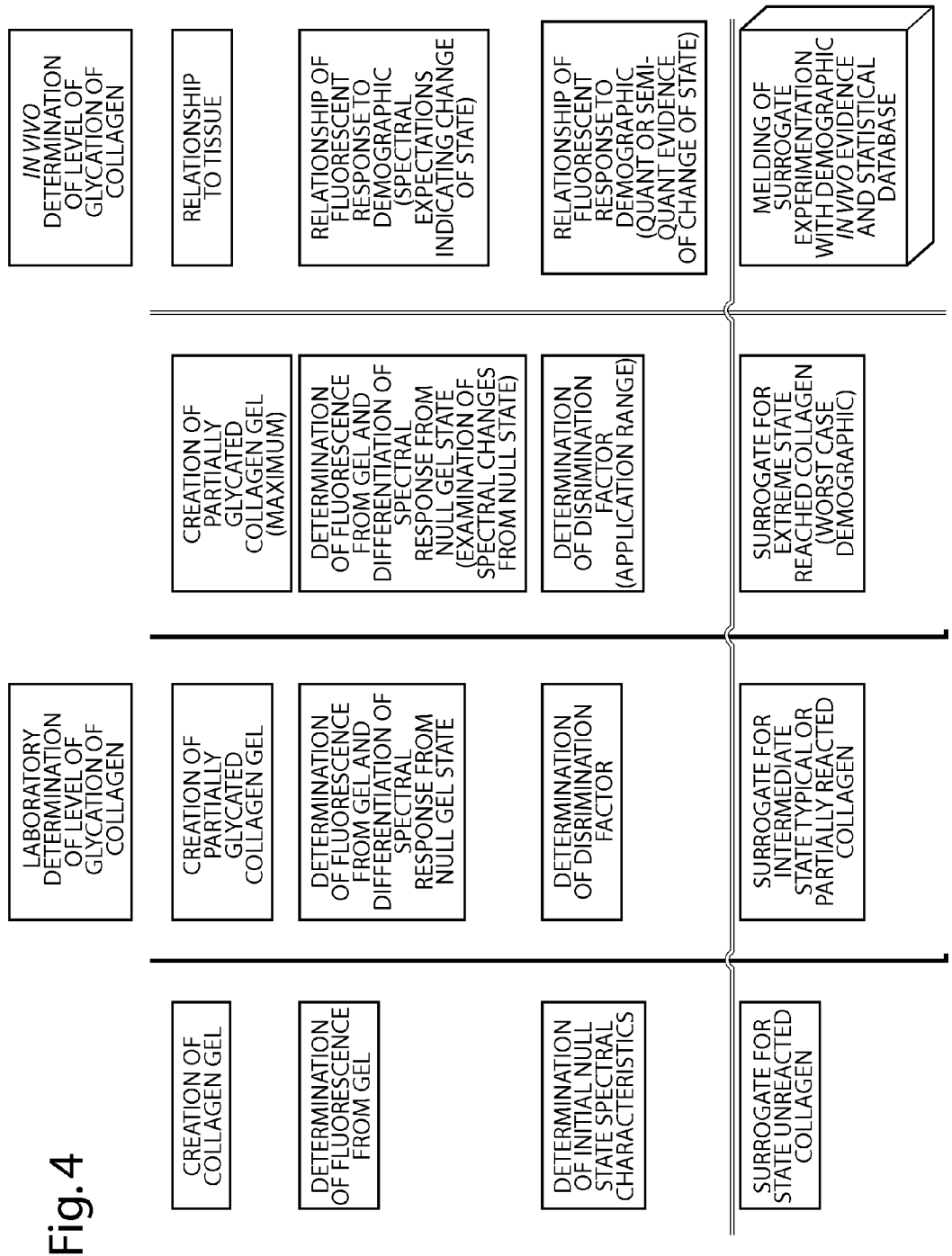
FIG. 4 is a schematic representation of a method for evaluating levels of glycation in collagen gels including surrogate testing with in vivo testing.

To further illustrate the present invention, FIGS. 3-4 illustrate the development of a glycation evaluation method including both a laboratory determination of the level of the glycation of collagen, as well as an in vivo determination of the glycation of collagen. As shown in FIGS. 3-4, the method includes the creation of a non-glycated collagen gel, a partially glycated collagen gel, and a collagen gel having maximum glycation. For each collagen gel, the current method includes a determination of the gel fluorescence. For the partially glycated collagen gel and the collagen gel having maximum glycation, this step also includes differentiating the spectral response from the null gel state, for example, an examination of the spectral changes from the null gel state, where the null state is determined from the fluorescence of the non-glycated collagen gel. The resulting fluorescent spectra constitute a surrogate for unreacted collagen, partially reacted collagen, and extreme or worse case reacted collagen.

As noted above, the method of FIGS. 3-4 can include an in vivo determination of the glycation of collagen. This can include the determination of the fluorescent response of skin tissue of a subject sample, as well as the determination of a relationship between the fluorescent response and a particular demographic, if any. By melding the results of the in vivo spectral response with the results of the surrogate experimentation of the collagen gels, the present method can achieve a statistical basis for determining the efficacy of future collagen gels, as well as their effectiveness as an anti-aging ingredient. For example, the present method can achieve a statistical basis for unreacted collagen, partially reacted collagen, and extremely reacted collagen, both in gel form and in the human skin.

FIGS. 3-4 illustrate a laboratory and in vivo fluorescent determination of the levels of glycation of collagen. The laboratory and in vivo analysis of FIGS. 3-4 include the creation of a non-glycated collagen gel, a partially glycated collagen gel, and a collagen gel having maximum glycation. For each collagen gel, the present analysis includes a determination of gel fluorescence. For all but the non-glycated collagen gel, the analysis includes differentiating the spectral response from the null gel state. This can include an examination of the spectral changes from the null gel state, where the null gel state is determined from the fluorescence of the non-glycated collagen gel. The resulting spectra for each gel provide a surrogate for unreacted collagen, partially reacted collagen, and extreme or worse case reacted collagen. In addition to the laboratory determination of glycation in collagen gel, the analysis includes the in vivo determination of the glycation of collagen. This can include the determination of the fluorescent response of skin tissue of a subject, as well as the determination of a relationship between a fluorescent response and a particular demographic, if any. By melding the results of the in vivo spectral acquisition with the results of the surrogate experimentation of the collagen gels, the present method can achieve a statistical basis for determining the efficacy of future collagen gels, as well as their effectiveness as anti-aging ingredients. For example, the present method can achieve a statistical basis for an unreacted collagen, a partially reacted collagen, and an extremely reacted collagen, both as a gel and in the human skin.

The method of FIGS. 3-4 can also include a number of determinations. For example, the present method can include: a determination of the fluorescent response range from a selected demographic (designated "A" in FIG. 3); a determination of the fluorescence response average from a selected demographic (designated "B" in FIG. 3); a determination of the upper and lower limits of expected change due to supplemental use of a topical application (designated "C" in FIG. 3); a determination of wavelength responses for the overall demographic (designated "D" in FIG. 3); and a determination of the "best case" reproducibility of skin testing in vitro or in vivo (designated "E" in FIG. 3). The determination of the fluorescence response average can form a basis for positive or negative change due to a supplemental modification in a gel. The determination of the upper and lower limits can form a basis to determine the discrimination capacity for the fluorescence technique in the "best case" scenario, that is, a "go/no go" triage for the existing technique. The determination of wavelength response can form a basis for determining potential deconvolution of effects through comparison of response at varying excitation and emission wavelengths.

Figure 5A:
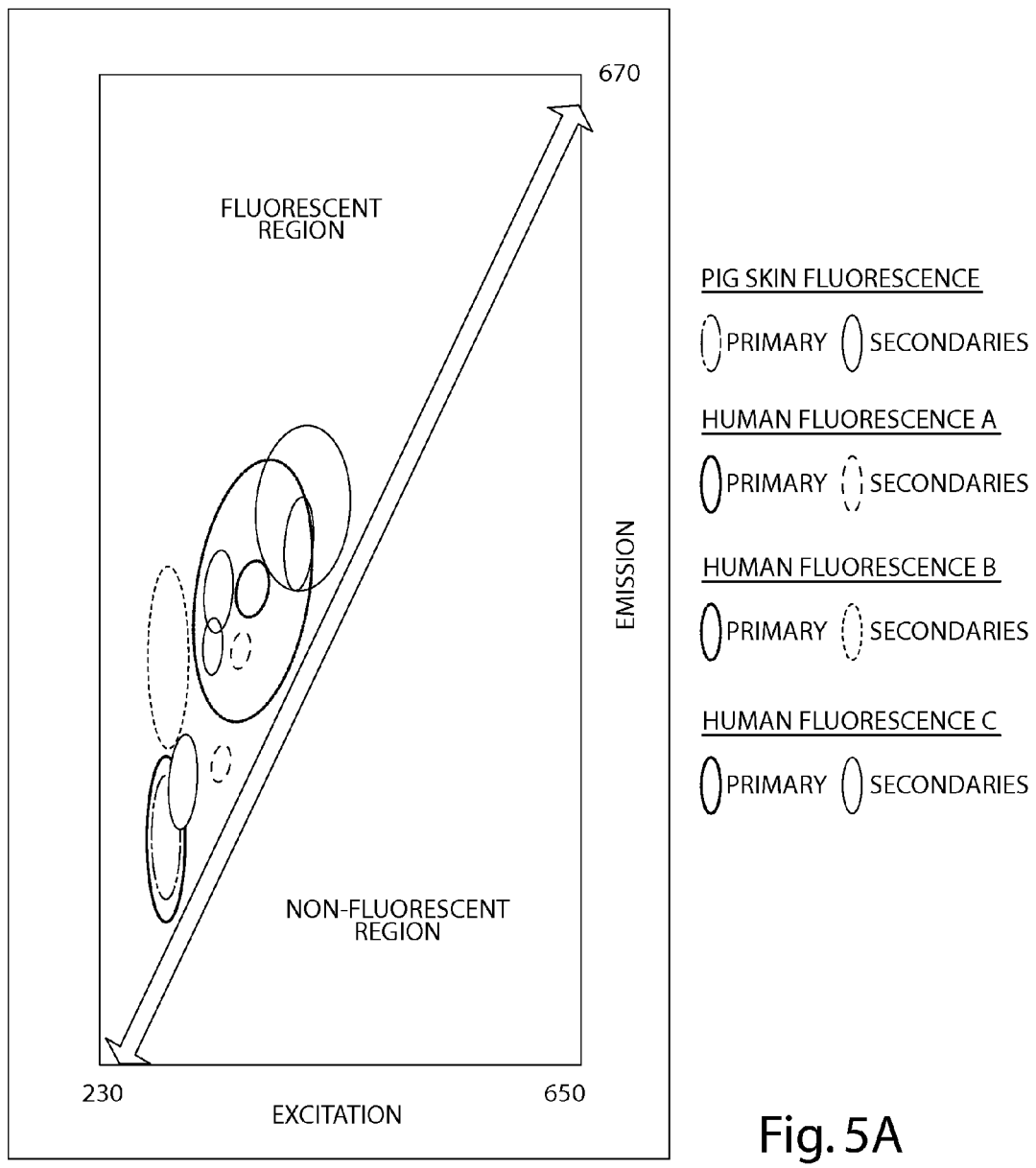
FIGS. 5A-5B are two-dimensional false color plots of the fluorescence spectrum of porcine skin and human skin.
Figure 5B:
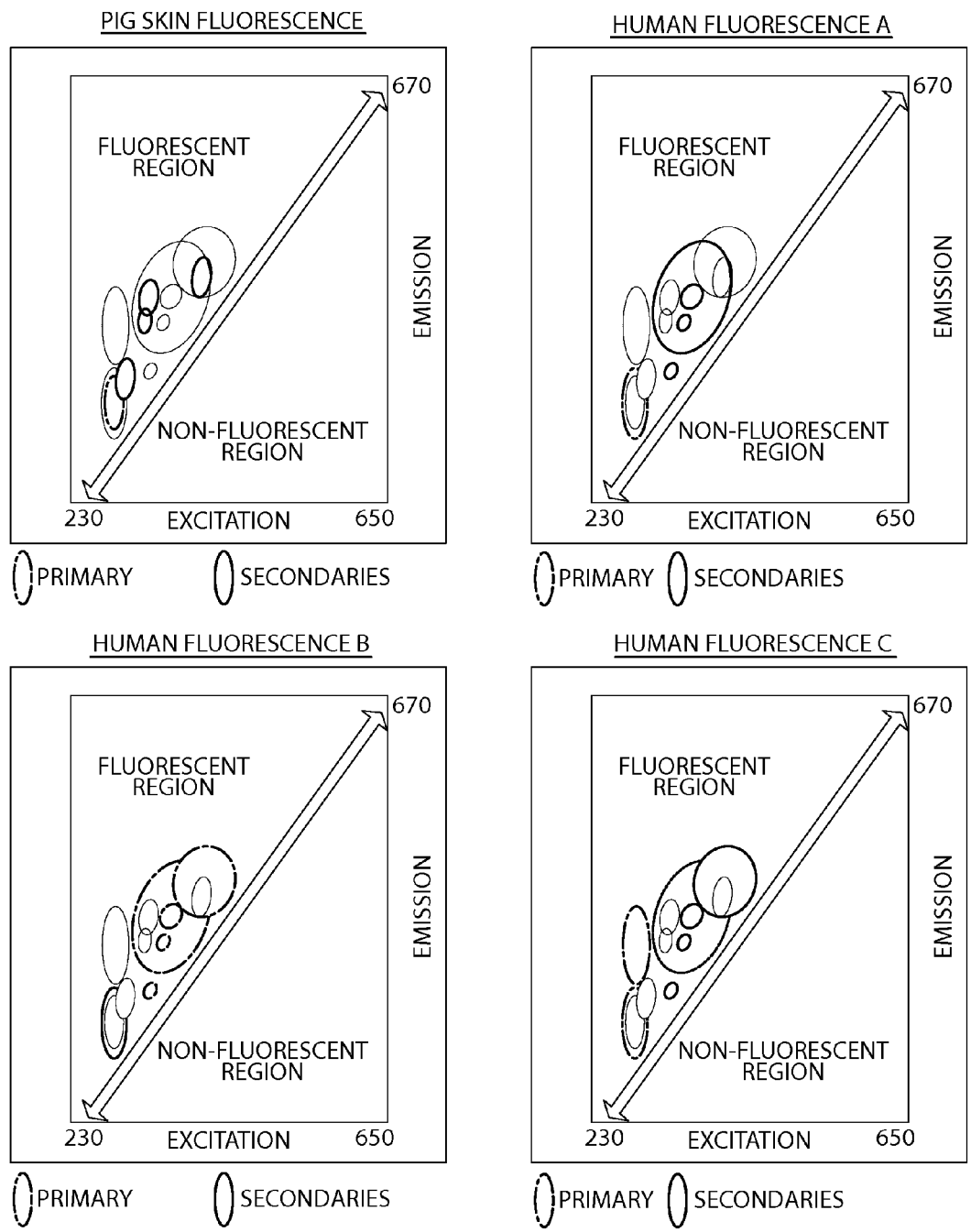
Figure 6A:
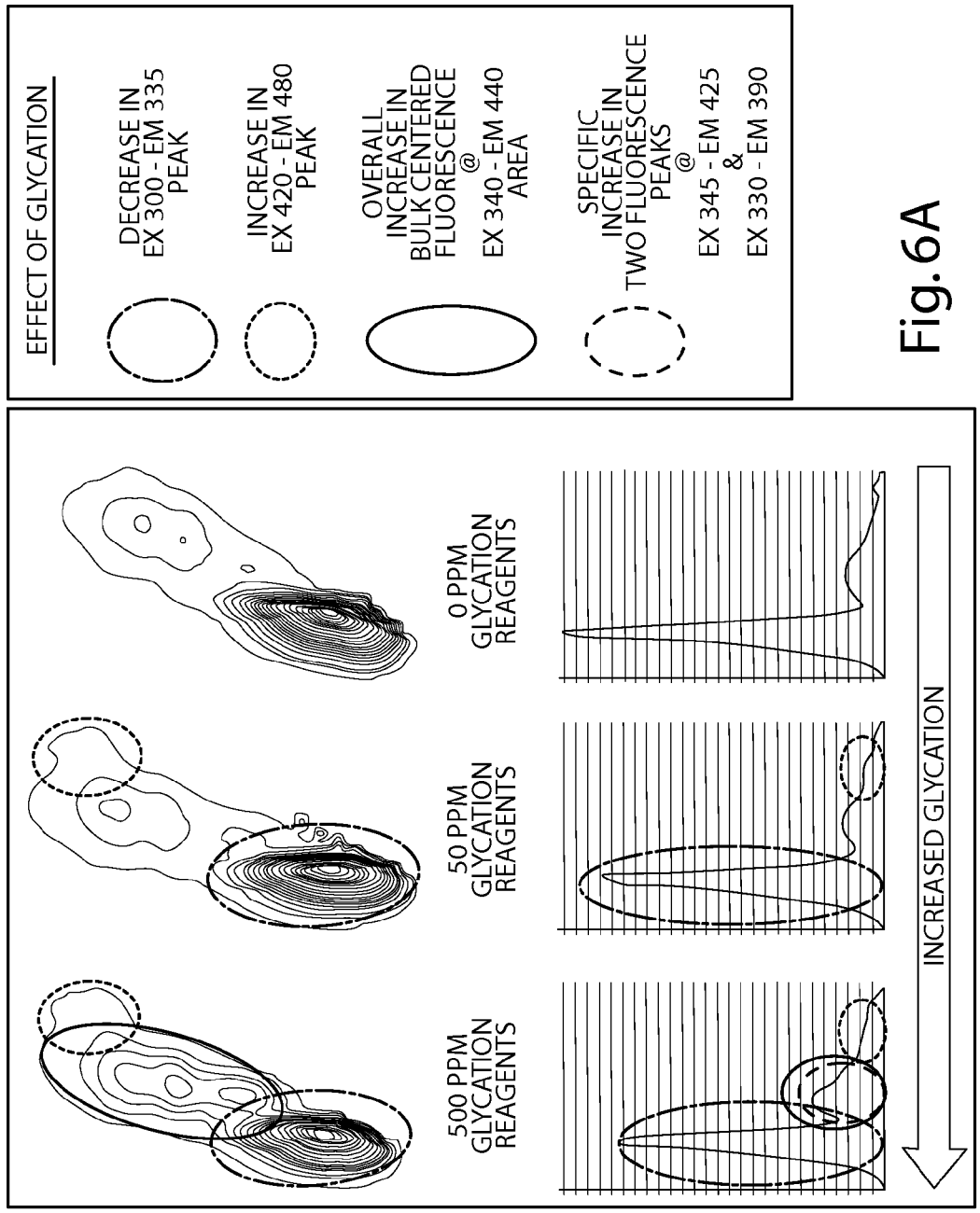
FIGS. 6A-6B are two- and three-dimensional false color plots illustrating the effect of glycation on the fluorescence spectrum of a human skin sample.
Figure 6B:
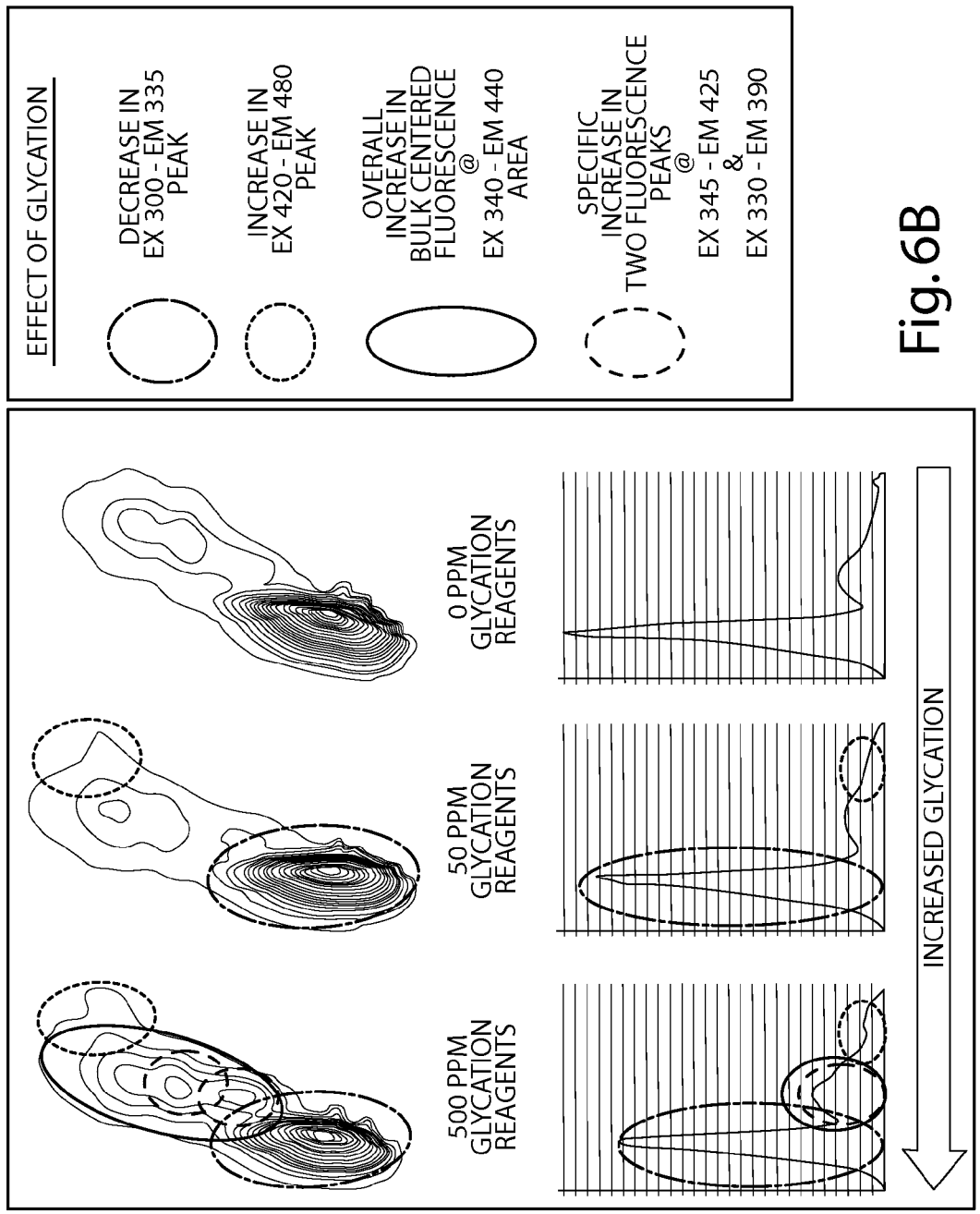

FIGS. 5A-5B illustrate the fluorescent spectrum of a porcine skin and a human skin. In particular, FIG. 5A includes a composite two-dimensional false color plot for a porcine sample and three human samples, while FIG. 5B includes separate spectral acquisitions for each sample. Each sample includes a primary and a secondary region of interest corresponding to a regional fluorescent peak for glycated collagen. Each region of interest corresponds to an excitation wavelength of between 230-650 nm and an emission wavelength of between 650-670 nm. Though shown as having two regions of interest, the spectral acquisition can include three or more regional fluorescent peaks relating to glycated collagen. For example, FIGS. 6A-6B illustrate two- and three-dimensional false color plots having in some instances four regional fluorescent peaks. As also shown in FIGS. 6A-6B, the emission intensity for each fluorescent region increases or decreases in response to increased glycation. For example, the primary fluorescent region includes an initial excitation wavelength of 300 nm and an initial emission wavelength of 335 nm. In response to the stepped addition of glycation reagents (0 ppm, 50 ppm and 500 ppm), this fluorescent region exhibited a measured decrease in fluorescent intensity. The remaining fluorescent regions actually increased in response to the addition of glycation reagents, including an overall increase at the following regions: 420 nm excitation and 480 nm emission; 340 nm excitation and 440 nm emission; 345 nm excitation and 425 nm emission; and 330 nm excitation and 390 nm emission.

FIG. 7 (referenced above) is a two-dimensional false color plot of a fluorescent spectrum of human subject. The false color plot can be analyzed pursuant to the methods set forth above in combination with fluorescent data from multiple human subjects. The use of pattern recognition for the identification of differences can provide a rapid and objective evaluation of multiple subjects, resulting in ingredient selection without invasive procedures, and potentially reducing the costs to researchers. Also, the use of selected regions of interest can reduce subject contact time, and can reduce regression time for the mathematical analysis of Part II. The fluorescent regions selected for analysis are generally representative of glycation and crosslinking in subject populations identified to have both normal and elevated glycation crosslinking.

EXAMPLE

The present example relates to the development of a glycation evaluation method to support in vivo ingredient screening. Diabetic and normal populations, representing elevated crosslinked collagen and normal crosslinked collagen respectively, were evaluated using a fiber-optic probe spectrofluorometer across a broad spectral range (230-480 nm excitation and 300-540 nm emission) while avoiding the primary reflection spectral ranges. Normalized maximum fluorescent intensities extracted from subset spectral ranges were obtained from the left and right forearms and the lower back of each subject and were evaluated for equivalence and proximity relationships. The resulting evaluation provided relationship patterns capable of identifying greater than 70% of the subjects as diabetic or non-diabetic in a blind study. Identifications were compared to study subject HbA1c and blood glucose levels obtained at the start of the study.

As noted above, increases in crosslinked collagen are associated with the aging process. The demand for improved skin care products generally benefits from the development of new and effective skin care formulations. The present embodiments can assist in the prediction of new ingredient efficacy. In particular, the present embodiments provides a low-cost method for determining the effectiveness of glycation-breaking or glycation-preventing active ingredients in skin care products.

The above description is that of current embodiments of the invention. Various alterations and changes can be made without departing from the spirit and broader aspects of the invention as defined in the appended claims, which are to be interpreted in accordance with the principles of patent law including the doctrine of equivalents. Any reference to claim elements in the singular, for example, using the articles "a," "an," "the" or "said," is not to be construed as limiting the element to the singular.

The invention claimed is:

1. A method for topical skin treatment evaluation, the method comprising:
    illuminating the skin area of each of a plurality of human subjects at a plurality of excitation wavelengths;
    detecting peak skin fluorescence levels for each of the plurality of human subjects at a plurality of emission wavelengths having a first emission wavelength and a second emission wavelength, each of the plurality of emission wavelengths corresponding to fluorophores of at least one of a glycated protein and an advanced glycated end-product;
    applying a regimen of a topical anti-glycation skin treatment to a skin area of at least one of the plurality of human subjects;
    after application of the regimen of the topical anti-glycation skin treatment, illuminating the skin area of each of the plurality of human subjects at the plurality of excitation wavelengths;
    detecting a change over time in the intensity of the peak skin fluorescence levels at the first emission wavelength and at the second emission wavelength, the change including an increase in intensity at the first emission wavelength and a decrease in intensity at the second emission wavelength;
    determining relative levels of skin glycation for each of the plurality of human subjects based at least partially on the detected change in intensity of the peak skin fluorescence levels of the first emission wavelength and the second emission wavelength; and
    evaluating the efficacy of the topical anti-glycation skin treatment based at least partially on the relative skin glycation levels for each of the plurality of human subjects.

2. The method of claim 1 wherein determining relative levels of skin glycation includes normalizing the detected peak skin fluorescence levels for each of the plurality of subjects.

3. The method of claim 2 wherein determining relative levels of skin glycation includes ranking the normalized peak skin fluorescence levels for each of the plurality of subjects.

4. The method of claim 3 wherein evaluating the efficacy of the skin treatment includes determining a proximity relationship for at least two of the plurality of human subjects.

5. The method of claim 1 wherein evaluating the efficacy of the topical treatment includes comparing the relative glycation level of each of the plurality of human subjects with whether each human subject received the regimen of the topical anti-glycation skin treatment.

6. A method comprising:
    providing an area of skin on each of a plurality of human subjects, at least one area of skin of the plurality of human subjects having been selectively treated with a topical anti-glycation skin treatment composition;
    radiating the at least one area of skin over a plurality of ranges of excitation wavelengths;
    detecting a peak fluorescence level of the areas of skin within a corresponding range of emission wavelengths for each of the plurality of ranges of excitation wavelengths, wherein the peak fluorescence levels correspond to at least one of a glycated protein and an advanced glycated end-product;
    detecting a change in intensity of the peak fluorescence levels over time, the change including an increase in intensity at a first one of the peak fluorescence levels and a decrease in intensity at a second one of the peak fluorescence levels;
    determining the relative levels of skin glycation of the human subjects from the detected change in intensity of the peak fluorescence levels of the skin areas for each of the plurality of ranges of emission wavelengths; and
    evaluating the efficacy of the topical anti-glycation skin treatment composition in at least one of preventing and reducing relative levels of skin glycation associated with the at least one area of skin of at least one of the plurality of human subjects having been selectively treated with the topical anti-glycation skin treatment composition.

7. The method of claim 6 wherein one of the ranges of excitation wavelengths is between 285 nm-310 nm, and the corresponding emission wavelength range is between 330 nm-365 nm.

8. The method of claim 6 wherein one of the ranges of excitation wavelengths is between 325 nm-350 nm, and the corresponding emission wavelength range is between 375 nm-405 nm.

9. The method of claim 6 wherein one of the ranges of excitation wavelengths is between 330 nm-370 nm, and the corresponding emission wavelength range is between 415 nm-440 nm.

10. The method of claim 6 wherein one of the ranges of excitation wavelengths is between 345 nm-385 nm, and the corresponding emission wavelength range is between 450 nm-475 nm.

11. The method of claim 6 wherein the peak fluorescence within at least one of the emission wavelength ranges proportionately increases with increased glycation.

12. The method of claim 6 wherein the peak fluorescence within at least one of the emission wavelength ranges proportionately decreases with increased glycation.

13. The method of claim 6 wherein a peak fluorescence within a first of the emission wavelength ranges proportionately decreases with increased glycation, and a peak fluorescence within a second of the emission wavelength ranges proportionately increases with increased glycation.

14. A method comprising:
  radiating the skin area of the plurality of human subjects over an excitation wavelengths range;
  detecting initial peak fluorescence levels of the skin areas within an emission wavelength range, the initial peak fluorescence levels corresponding to fluorophores of at least one of a glycated protein and an advanced glycated end-product;
  administering a regimen of a topical anti-glycation skin treatment to a skin area of at least one of the plurality of human subjects;
  after application of the regimen of the topical anti-glycation skin treatment, detecting changes over time to the initial peak fluorescence levels of the skin areas of the plurality of human subjects including an increase in intensity at a first one of the initial peak fluorescence levels and a decrease in intensity at a second one of the initial peak fluorescence levels;
  normalizing the detected peak fluorescence levels from after application of the regimen of the topical anti-glycation skin treatment for each of the plurality of human subjects;
  assessing relative glycation levels for each of the plurality of human subjects based at least in part on a ranking of the normalized fluorescence levels and based on the increase in intensity and the decrease in intensity of the first and second peak fluorescence levels, respectively; and
  evaluating the efficacy of the topical anti-glycation skin treatment in at least one of preventing and reducing skin glycation.

15. The method of claim 14 comprising:
  administering to at least another of the plurality of human subjects a placebo control.

16. The method of claim 15 comprising:
  comparing the relative glycation level of each of the plurality of human subjects with whether each human subject received the regimen of the topical anti-glycation skin treatment or the placebo control; and
  evaluating the efficacy of the topical anti-glycation skin treatment from the comparison of the relative skin glycation levels.

* * * * *